(12) United States Patent
Joy

(10) Patent No.: US 7,236,092 B1
(45) Date of Patent: Jun. 26, 2007

(54) PASSIVE SENSOR TECHNOLOGY INCORPORATING ENERGY STORAGE MECHANISM

(76) Inventor: James A. Joy, 320 Northpoint Pkwy., Ste P, Acworth, GA (US) 30102

( * ) Notice: Subject to any disclaimer, the term of this patent is extended or adjusted under 35 U.S.C. 154(b) by 149 days.

(21) Appl. No.: 10/923,763

(22) Filed: Aug. 23, 2004

Related U.S. Application Data

(60) Provisional application No. 60/598,078, filed on Aug. 2, 2004.

(51) Int. Cl.
*G08B 1/08* (2006.01)
*H04Q 7/00* (2006.01)

(52) U.S. Cl. .............................. 340/539.12; 340/572.1; 600/300

(58) Field of Classification Search ............ 340/539.12
See application file for complete search history.

(56) References Cited

U.S. PATENT DOCUMENTS

| | | | |
|---|---|---|---|
| 2,899,546 A * | 8/1959 | Hollmann .................... 342/50 |
| 3,432,852 A * | 3/1969 | Arnold ......................... 342/44 |
| 4,265,252 A * | 5/1981 | Chubbuck et al. .......... 600/561 |
| 4,660,568 A * | 4/1987 | Cosman ...................... 600/561 |
| 5,339,051 A | 8/1994 | Koehler et al. |
| 5,491,604 A * | 2/1996 | Nguyen et al. ............. 361/278 |
| 5,619,997 A | 4/1997 | Kaplan |
| 6,025,725 A * | 2/2000 | Gershenfeld et al. ....... 324/652 |
| 6,046,668 A * | 4/2000 | Forster .................... 340/572.2 |
| 6,111,520 A | 8/2000 | Allen et al. |
| 6,278,379 B1 * | 8/2001 | Allen et al. ............ 340/870.16 |
| 6,312,380 B1 * | 11/2001 | Hoek et al. ................. 600/437 |
| 6,461,301 B2 | 10/2002 | Smith |
| 6,600,252 B2 * | 7/2003 | Nguyen ...................... 310/309 |
| 6,744,174 B2 | 6/2004 | Paden et al. |
| 6,819,246 B1 * | 11/2004 | Seppa ...................... 340/572.7 |
| 6,870,461 B2 * | 3/2005 | Fischer et al. ........... 340/572.1 |

* cited by examiner

*Primary Examiner*—Benjamin C. Lee
*Assistant Examiner*—Eric M. Blount
(74) *Attorney, Agent, or Firm*—William B. Noll

(57) ABSTRACT

A passive sensor system having the capacity to respond to a variety of stimuli in the form of pulses of a specified frequency. The system includes a sensor operatively connected to an LC circuit characterized by a quality factor (Q) of less than 200, and a high Q resonator having a Q greater than 200.

8 Claims, 4 Drawing Sheets

Prior Art LCR Sensor

PASSIVE SENSOR TECHNOLOGY INCORPORATING ENERGY STORAGE MECHANISM

This application is related to and claims priority of Provisional Application Ser. No. 60/598,078, filed Aug. 2, 2004, by the inventor hereof and under the same title.

FIELD OF THE INVENTION

This invention is directed to the field of sensor detection technology, specifically for measuring the presence, verifying the operation of remote sensors, and communicating certain information from said sensors such as may be placed in the human body. These sensors measure various bodily functions, such as blood pressure, heart rate, and other critical systems. These sensors may also be used in military, commercial and industrial applications where sensors are used to monitor sensitive applications requiring the return of measured information to the interrogating device.

BACKGROUND OF THE INVENTION

The present invention relates to Passive LCR (Inductor, Capacitor, Resistor), or simply LC, sensors. These sensors are widely used in the medical, industrial, military, and commercial applications. These passive sensors respond to various stimuli. These stimuli are often in the form of specific pulses, multiple pulses of that specific frequency, various pulses at different intervals and frequencies, a "white noise" consisting of a pseurandom signal, a Carrier Wave (CW) combined with "white noise", a combination of AM or PM frequency, or a Carrier Wave transmitted at a specific or variable frequencies. Each of these stimuli is designed to result in a different response from the Passive LCR sensor. The capacity to accept multiple signals from disparate sources greatly enhances the features and functions of these passive sensors. The enhancements include but are not limited to: greater range, greater detection, greater operation efficiency, better and more effective communication with the devices that measure the sensors.

There are several prior art attempts related to sensors and circuits, where such attempts are detailed in the following U.S. patents:

a.) U.S. Pat. No. 4,265,252 to Chubbuck teaches an implantable transensor device containing a passive RF resonant circuit having a natural frequency influenced by the pressure of the sensor's environment in a body cavity of a living entity. The circuit of the transensor includes an inductor and a capacitor, at least one of which varies in value in direct relation to variation of environmental pressure to change the resonant frequency of the circuit. The circuit can be externally interrogated to determine the resonant frequency thereof at any point in time by the imposition thereon of swept frequency electromagnetic radiation provided by a monitoring device which determines when some of the radiation is absorbed as a result of the frequency of the radiation being the same as the resonant frequency of the transensor circuit. An imposed relationship exists between the sensed environmental pressure, and the reactance of the reactive components of the circuit. A natural relationship exists between pressure sensitive reactance, and the resonant frequency of the circuit. As a result, an increase in environmental pressure causes a corresponding increase in frequency and a decrease in environmental pressure causes a decrease in frequency.

b.) U.S. Pat. No. 5,619,997 to Kaplan teaches a passive sensor system utilizing ultrasonic energy is disclosed. The passive sensor system includes at least one ultrasonically vibratable sensor and an ultrasonic activation and detection system. The sensor has at least one vibration frequency which is a function of a physical variable to be sensed. The ultrasonic activation and detection system excites the sensor and detects the vibration frequency from which it determines a value of the physical variable. The sensor includes a housing, a membrane which is attached to the housing and which is responsive to the physical variable, a vibratable beam attached to the housing at one end and a coupler, attached to the membrane and to a small portion of the vibratable beam, which bends the vibratable beam in response to movement of the membrane.

c.) U.S. Pat. No. 6,744,174 to Paden, et al. is a frequency stability analysis and design method for frequency robust resonators, such as MEMS resonators, is presented. The frequency characteristics of a laterally vibrating resonator are analyzed. With the fabrication error on the sidewall of the structure being considered, the first and second order frequency sensitivities to the fabrication error are derived. A relationship between the proof mass area and perimeter, and the beam width, is developed for single material structures, which expresses that the proof mass perimeter times the beam width should equal six times the area of the proof mass. Design examples are given for the single material and multi-layer structures. The results and principles presented in the paper can be used to analyze and design other MEMS resonators.

d.) U.S. Pat. No. 6,461,301 to Smith relates to a resonance based pressure transducer system, insertable into a living body for the in vivo measurement of pressure. It comprises a pressure sensor (2) having a mechanical resonator (16), the resonance frequency of which is pressure dependent; and a source of ultrasonic energy (4). The sensor (2) is mechanically coupled to said source (4) of ultrasonic energy, and the sensor and the source of ultrasonic energy are provided on a common, elongated member (6) at the distal end thereof. A system for pressure measurement comprises an AC power supply, a resonance based pressure transducer system, and a control unit for controlling the supply mode of the AC power, and for analyzing a resonance signal emitted from the resonance based pressure transducer system.

e.) U.S. Pat. No. 5,339,051 to Koehler, et al. discloses a micro-miniature resonator-oscillator. Due to the miniaturization of the resonator-oscillator, oscillation frequencies of one MHz and higher are utilized. A thickness-mode quartz resonator housed in a micro-machined silicon package and operated as a "telemetered sensor beacon" that is, a digital, self-powered, remote, parameter measuring-transmitter in the FM-band. The resonator design uses trapped energy principles and temperature dependence methodology through crystal orientation control, with operation in the 20-100 MHz range. High volume batch-processing manufacturing is utilized, with package and resonator assembly at the wafer level. Unique design features include squeeze-film damping for robust vibration and shock performance, capacitive coupling through micro-machined diaphragms allowing resonator excitation at the package exterior, circuit integration and extremely small (0.1 in. square) dimensioning. A family of micro-miniature sensor beacons is also disclosed with widespread applications as biomedical sensors, vehicle status monitors and high-volume animal identification and health sensors. The sensor family allows measurement of temperatures, chemicals, acceleration and pressure. A microphone and clock realization is also available.

f.) U.S. Pat. No. 6,111,520 to Allen, et al teaches that several sensors are provided for determining one of a number of physical properties including pressure, temperature, and other physical conditions. In general, the sensors feature a resonant circuit with an inductor coil which is electromagnetically coupled to a transmitting antenna. When an excitation signal is applied to the antenna, a current is induced in the sensor circuit. This current oscillates at the resonant frequency of the sensor circuit. The resonant frequency and bandwidth of the sensor circuit is determined using an impedance analyzer, a transmitting and receiving antenna system, or a chirp interrogation system. The resonant frequency may further be determined using a simple analog circuit with a transmitter. The sensors are constructed so that either the resonant frequency or bandwidth of the sensor circuit, or both, are made to depend upon the physical properties such as pressure, temperature, presence of a chemical species, or other condition of a specific environment. The physical properties are calculated from the resonant frequency and bandwidth determined.

The manner by which the present invention increases the range of the sensor increases the means and number of communication methods increases the sensitivity of detection, and increases the reliability of communications all of which will become more apparent in the description which follows, especially in conjunction with the accompanying drawings.

SUMMARY OF THE INVENTION

The invention teaches a technology that incorporates a high Q resonator with normal LC circuits, and enables the sensor to store energy. This stored energy returns a stable Radio Frequency (RF) signal to the LC circuit, for a much longer period of time than would be afforded by relatively low Q LC circuits alone, along with any phase modulation added by the LC circuit.

In another embodiment, the high Q resonator could itself be tunable (see FIG. 4), thereby providing the storage of RF energy whose frequency is dependent on some measured parameter, such as pressure or various bodily functions. In this case the phase modulation offered by tuning the LC circuit may or may not be utilized.

Presently, all passive sensors of the LCR or LC types have a predetermined bandwidth for communication with external devices. Q is proportional to the inverse of the amount of energy dissipated in the LC circuit. The present invention incorporates a high Q (>200) resonator with a standard LC circuit, which typically has a low Q (<200) rating. The high resonator allows the sensor to store energy when the circuit is stimulated via the external interrogating device. This storage of energy allows the resonator to return stable Radio Frequency (RF) signal to the LC circuit for a much greater amount of time than is normal for the LC circuits alone. The present invention provides several significant advances over the prior art by increasing the range of sensing activity, increasing the means and number of communication methods, increasing the sensitivity of detection, allowing the use of multiple sensors in a localized area, allowing simplification of the interrogation methods, and increasing the reliability of communications.

Accordingly, a feature of the invention is the provision either in the ability to detect a sensor or extend the range of detection, the ability to resolve its operating frequency, the ability to convey modulation, ability to operate multiple sensors in closer proximity, the ability to resolve smaller changes in measured parameters.

A further feature of the invention is the use of a high Q resonator with a low Q LC circuit.

A further feature is the use of the high Q resonator returns a stable RF carrier to the LC circuit which radiates the RF signal along with any phase modulation added by the LC circuit.

A further feature is the ability to use a tunable high Q resonator thereby providing a frequency modulated signal source, whose frequency can be proportional to a measured parameter such as blood pressure or various bodily functions.

A further feature is the high Q resonator phase modulated by a tuning change in the LC circuit.

A further feature is that the resonator converts electrical RF energy to mechanical vibration.

A further feature is that the resonator converts mechanical vibration to electrical RF energy.

Another feature is that by utilizing this approach to sensor design, simpler interrogation methods may be used.

These and other features of the invention will become more apparent in the further description, especially when read in conjunction with the accompanying drawings.

DETAILED DESCRIPTION OF THE PREFERRED EMBODIMENT

The invention teaches a technology that incorporates a high Q resonator with a normal LC circuits, and enables the sensor to store energy for a much longer period of time than would normally be possible. This stored energy returns a stable Radio Frequency (RF) signal to the LC circuit along with any phase modulation added by the LC circuit.

Presently, all passive sensors of the LCR or LC types have a predetermined bandwidth for communication with external devices. The center operating frequency of the circuit divided by the bandwidth yields the Q or Quality factor. If a device has a limited Q factor, the communication reliability and performance of the device is limited. Q is proportional to the inverse of the amount of energy dissipated in the LC circuit. The present invention incorporates a high Q resonator with a standard LC circuit, which typically has a low Q rating. This unique feature of a resonator with a high Q factor with a standard LC circuit allows the circuit to store the energy for a much greater amount of time when the circuit is externally stimulated, and return a portion of that stored energy back to the LC circuit, for a much greater amount of time, which creates a circulating current.

When it is desired to transmit information from the high Q resonator to the LC circuit, the LC circuit behaves as a phase modulator, and acts as a radiating device to transmit a return signal. The combination of the resonator with the high Q and the LC circuit returns energy during the transmittal process. This returned energy persists for a period of time which returns the stable RF signal to the circuit which radiates the signal along with any phase modulation added by the circuit. The period of time this RF signal will persist is dependent on the chosen Q of the high Q resonator, as well as the coupling factors selected in the design process.

Figure 2:
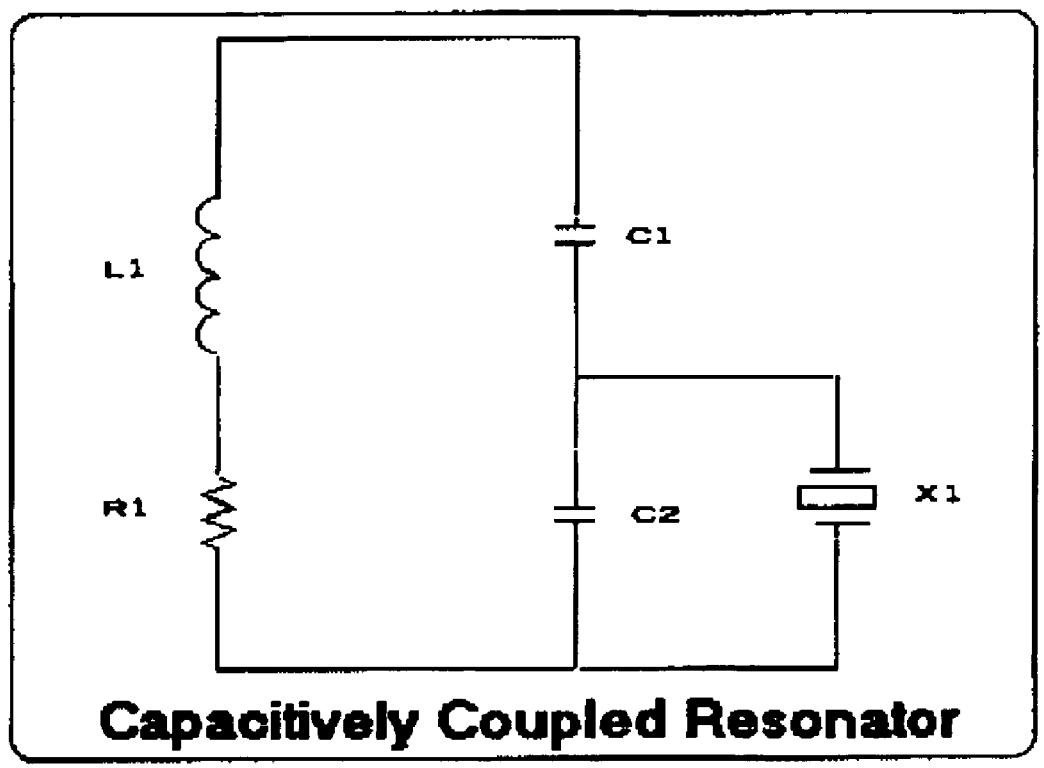
FIG. 2 shows a schematic representation of a capacitively modulated passive sensors. Tuning the capacitor in these circuit arrangements modulates the phase of the circulating current.
Figure 3:
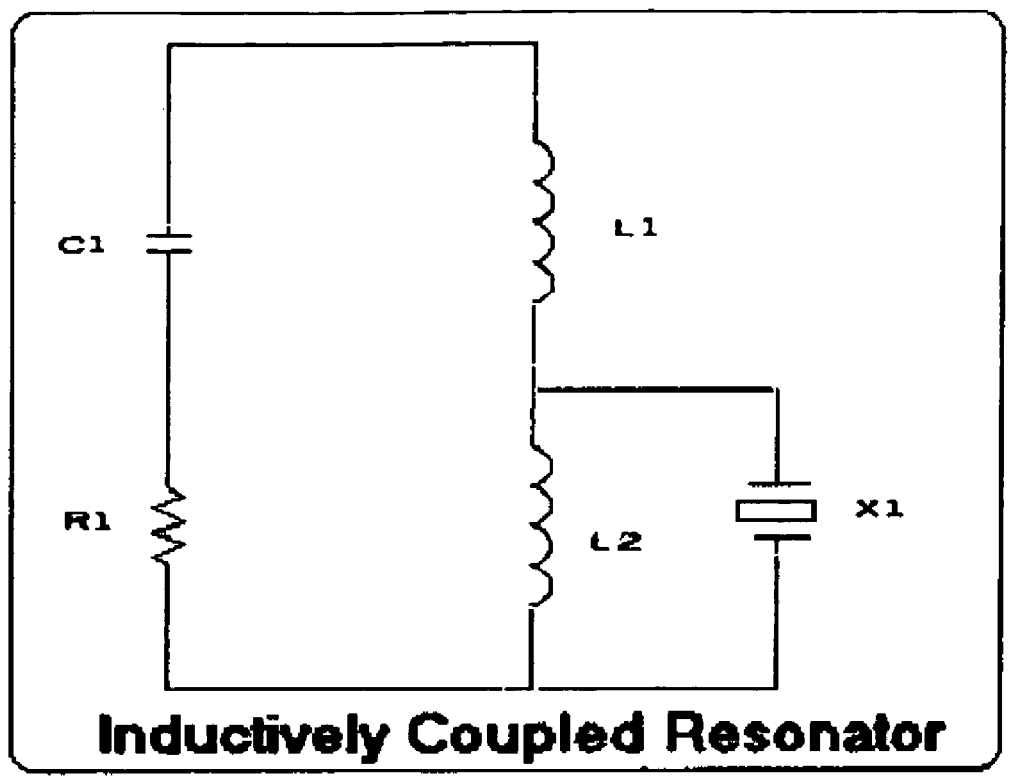
FIG. 3 shows a schematic representation of a inductively modulated passive sensors. Tuning the inductor in these circuits arrangements modulates the phase of the circulating current.
Figure 4:
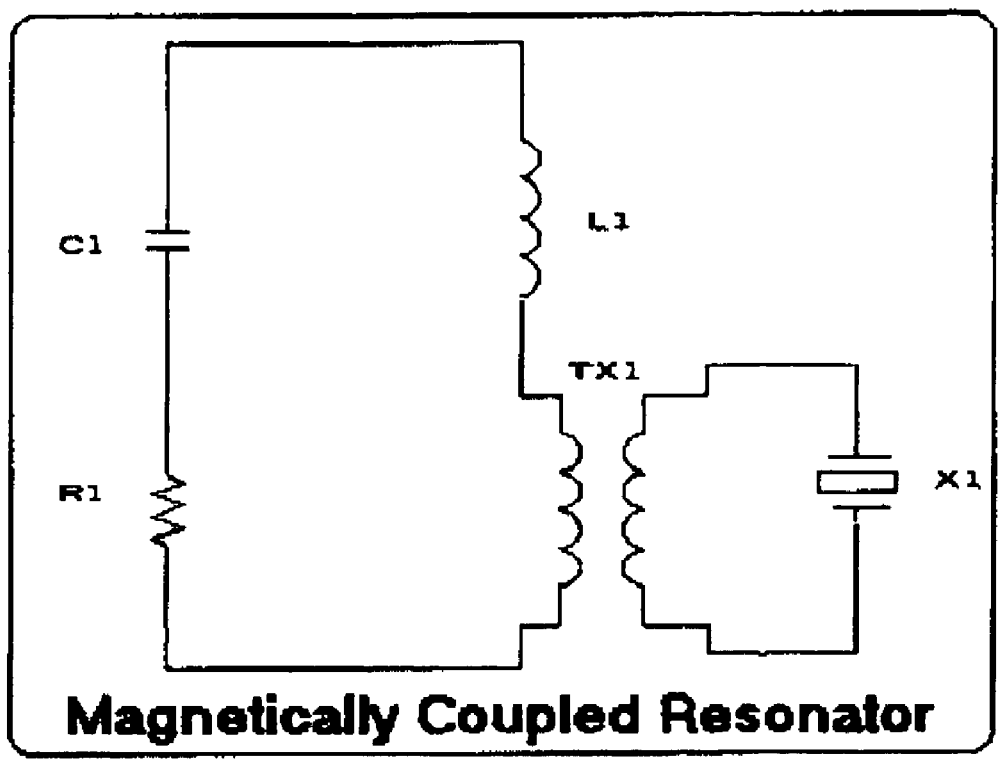
FIG. 4 shows a schematic representation of a resonator passive sensors. Tuning the resonators in these circuits arrangements modulates the frequency of the stored RF energy.

If the LCR portion of the circuit is tuned over a range of frequencies, the sustaining signal from the high Q resonator will be phase modulated by the tuning change, as shown in FIGS. 2 and 3. This allows the modification of the inductive (L1) or capacitive (C1) portion of the LC circuit by some parameter such as pressure, or temperature. Once this modification is enacted, the signal becomes a phase modulated RF signal. If the high Q resonator portion of the circuit (X1) is tuned over a range of frequencies, the sustaining signal from the high Q resonator will be frequency modulated by the tuning change, as shown in FIG. 4. This allows the modification of the high Q resonator portion of the sensor circuit by some parameter such as pressure, or temperature. Once this modification is enacted, the signal becomes a frequency modulated RF signal.

Figure 1:
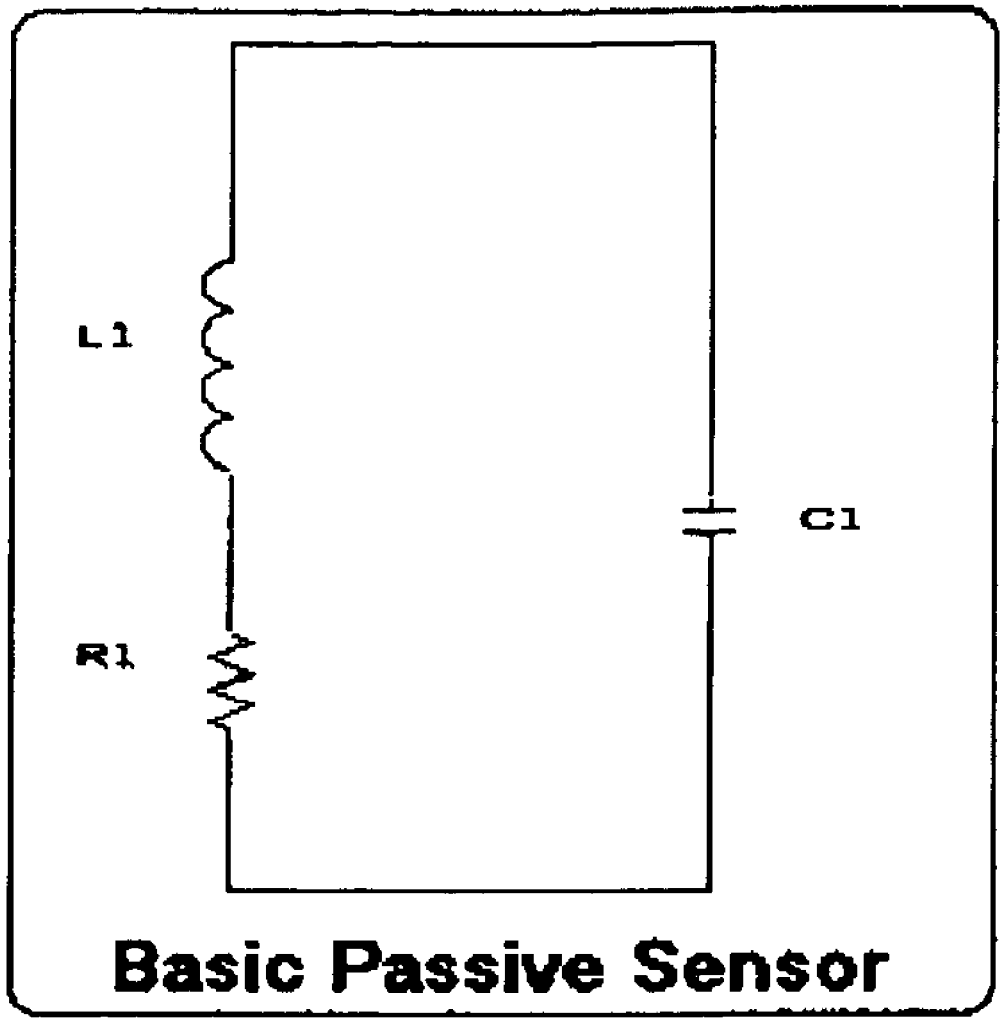
FIG. 1 shows a schematic representation of a standard passive sensor, and the different resonators coupled to that passive sensor. These include capacity coupled resonator, the magnetically coupled resonator, and the inductively coupled resonator.

Controlling and sustaining the Q of the sensor depends upon the coupling level between the LC circuits and the resonator. To maximize the efficiency and effectiveness of Q depends upon the different applications. The selection of this coupling level will directly affect how much energy is stored, and for how long this signal will persist. The coupling mechanism may be electrical magnetic, inductive, capacitive, or resistive. See FIG. 1.

The choice of a resonator type is flexible and can be used with a number of devices which has the ability to reversibly convert electrical RF energy into mechanical vibration. These include quartz crystals, MEMs resonators, dielectric resonators, and a (Surface Acoustical Wave) SAW device. In some cases the choice of an appropriate resonator may be dependent on the ability to alter its operating frequency based on some measured parameter, such as blood pressure.

It is recognized that changes, variations and modifications may be made to this invention, especially by those skilled in the art, without departing from the spirit and scope of the invention. Accordingly, no limitation is intended to be imposed thereon except as set forth in the accompanying claims.

I claim:

1. A passive sensor system having the capacity to respond to a variety of stimuli in the form of pulses of a specified frequency, said system including a.) a sensor operatively connected to an LC circuit having a quality factor (Q) of less than 200, where Q is the center operating frequency of the circuit divided by the bandwidth thereof; and, b.) a high Q resonator incorporated in said LC circuit, where said resonator has a Q greater than 200, whereby to allow said sensor to store energy when said circuit is stimulated by an external device, said system further including means for tuning said circuit over a range of frequencies, where the sustaining signal from said high Q resonator will be phase modulated by said tuning means.

2. The system according to claim 1, wherein said stored energy returns a stable radio frequency (RF) signal to said LC circuit.

3. The system according to claim 1, wherein controlling and sustaining the Q of said sensor depends upon the coupling level between said circuit and said high Q resonator, said coupling level may be taken from coupling mechanics selected from the group consisting of electrical, magnetic, inductive, capacitive, and resistive.

4. The system according to claim 1, wherein said high Q resonator has the ability to reversibly convert electrical RF energy into mechanical energy.

5. The system according to claim 1, wherein said high Q resonator is selected from the group of devices consisting of quartz crystals, MEMs resonators, dielectric resonators, and surface acoustical wave devices.

6. The system according to claim 5, wherein the selection of said high Q resonator is based on its ability to alter its operating frequency based on a desired measured parameter.

7. The system according to claim 6, wherein said sensor is operable to measure certain bodily functions.

8. A passive sensor system having the capacity to respond to a variety of stimuli in the form of pulses of a specified frequency, said system including a.) a sensor operatively connected to an LC circuit having a quality factor (Q) of less than 200, where Q is the center operating frequency of the circuit divided by the bandwidth thereof; and, b.) a high Q resonator incorporated in said LC circuit, where said resonator has a Q greater than 200, whereby to allow said sensor to store energy when said circuit is stimulated by an external device, wherein said stored energy returns a stable radio frequency (RF) signal to said LC circuit, and said high Q resonator has the capability to selectively transmit information to said LC circuit, where said LC circuit acts as a phase modulator, and as a radiating device to transmit a return signal.

* * * * *